United States Patent
Saunte et al.

(10) Patent No.: US 10,620,423 B2
(45) Date of Patent: Apr. 14, 2020

(54) METHOD OF EXAMINING AN EYE OF A SQUINTING PERSON BY USE OF A PERISCOPIC DEVICE AND SUCH A PERISCOPIC DEVICE

(71) Applicant: GeelTech ApS, Virum (DK)

(72) Inventors: Jon Peiter Saunte, Virum (DK); Max Bonne, Brøndby (DK); Thomas Olund Christensen, Kgs. Lyngby (DK)

(73) Assignee: GeelTech ApS, Virum (DK)

( * ) Notice: Subject to any disclaimer, the term of this patent is extended or adjusted under 35 U.S.C. 154(b) by 0 days.

(21) Appl. No.: 15/538,466

(22) PCT Filed: Dec. 22, 2015

(86) PCT No.: PCT/EP2015/080944
§ 371 (c)(1),
(2) Date: Jun. 21, 2017

(87) PCT Pub. No.: WO2016/102547
PCT Pub. Date: Jun. 30, 2016

(65) Prior Publication Data
US 2018/0003942 A1    Jan. 4, 2018

(30) Foreign Application Priority Data
Dec. 22, 2014    (EP) ...................................... 14199641

(51) Int. Cl.
*G02B 5/04*    (2006.01)
*G02B 23/08*    (2006.01)
(Continued)

(52) U.S. Cl.
CPC .............. *G02B 23/08* (2013.01); *A61B 3/085* (2013.01); *A61B 3/032* (2013.01)

(58) Field of Classification Search
CPC .......... G02B 23/08; G02B 5/04; G02B 5/045; G02B 7/1805; B60R 1/10; B60R 1/105;
(Continued)

(56) References Cited

U.S. PATENT DOCUMENTS 2,091,173 A    8/1937   Wottring
2,233,689 A    3/1941   Wildebush
(Continued)

FOREIGN PATENT DOCUMENTS

CN    101460885 A    6/2009
DE      3206530 A1    9/1983
(Continued)

OTHER PUBLICATIONS

Bibliographic Data for DE3206530A1 from Espacenet dated Sep. 21, 2017.
(Continued)

*Primary Examiner* — Stephone B Allen
*Assistant Examiner* — Jyotsna V Dabbi
(74) *Attorney, Agent, or Firm* — Woodard, Emhardt, Henry, Reeves & Wagner, LLP

(57) ABSTRACT

Disclosed is a periscopic device for examining an eye of a person with an inwardly squinting eye (esotropia). The periscopic device includes a tube with two mirrors arranged at opposite ends of the tube. The mirrors are arranged so that when the person looks through the periscopic device with the inwardly squinting eye, the two mirrors deflect the line of sight of the person toward an object reflected in the second mirror. To account for the squint of the eye, either a base out prism can be used to deflect the line of sight toward the first mirror, or the two mirrors can be arranged non-parallel to each other. With the inwardly squinting eye
(Continued)

focused on the reflected object, the other eye can be examined. Methods of using the periscopic device are also disclosed.

18 Claims, 5 Drawing Sheets

(51) Int. Cl.
　　*A61B 3/08*　　　(2006.01)
　　*A61B 3/032*　　(2006.01)
(58) Field of Classification Search
　　CPC ........... B60R 1/002; F41G 1/40; A61B 3/085; A61B 3/032
　　USPC .................................. 359/831, 402, 403, 405
　　See application file for complete search history.

(56) References Cited

U.S. PATENT DOCUMENTS

| | | | |
|---|---|---|---|
| 3,484,155 A | 12/1969 | Praeger et al. | |
| 4,150,875 A * | 4/1979 | Stachiw | G02B 23/08 114/340 |
| 6,055,098 A * | 4/2000 | Lett | G02B 23/08 359/402 |
| 6,101,048 A * | 8/2000 | Wheeler | B60R 1/10 359/726 |
| 8,797,648 B2 * | 8/2014 | Motahedy | B60J 3/06 359/488.01 |
| 2011/0085130 A1 | 4/2011 | Walsh | |

FOREIGN PATENT DOCUMENTS

| | | |
|---|---|---|
| EP | 1082939 A2 | 3/2001 |
| JP | 11155813 A | 6/1999 |
| JP | 2009539127 A | 11/2009 |
| JP | 2011078597 A | 4/2011 |
| JP | 2014083193 A | 5/2014 |

OTHER PUBLICATIONS

Guyton, et al, Remote Optical Systems for Ophthalmic Examination and Vision Research, Applied Optics, vol. 26, No. 8, Apr. 15, 1987.
International Search Report from related PCT/EP2015/080944 dated Mar. 23, 2016.
Written Opinion from related PCT/EP2015/080944 dated Mar. 23, 2016.
Chinese Office Action issued in related application No. CN201580076326.5 dated May 13, 2019.
Machine translation of JP2011078597A by Patent Translate European Patent Office on Nov. 8, 2019 (pp. 50).
Machine translation of JP2014083193A by Patent Translate European Patent Office on Nov. 8, 2019 (pp. 31).
Machine translation of JPH11155813A by Patent Translate European Patent Office on Nov. 8, 2019 (pp. 19).
Partial translation of Chinese Office Action issued in related application No. CN201580076326.5 dated May 13, 2019.
Partial translation of Japanese Office Action issued in related application No. JP2017-551028 on Oct. 4, 2019.

* cited by examiner

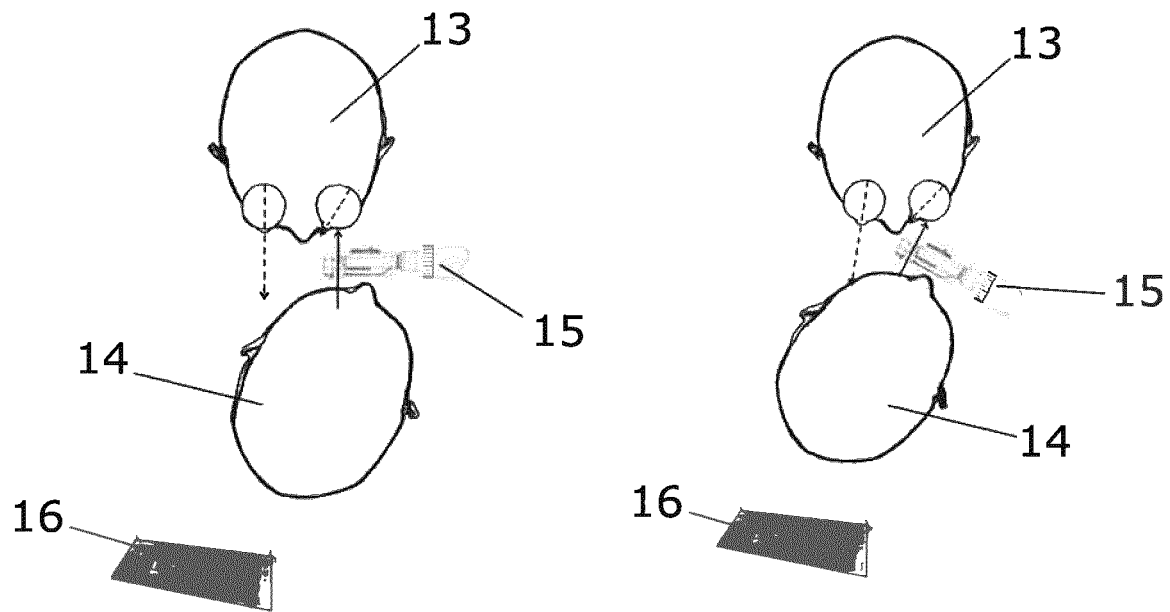
Fig. 2.a
Prior art
Fig. 2.b
Prior art
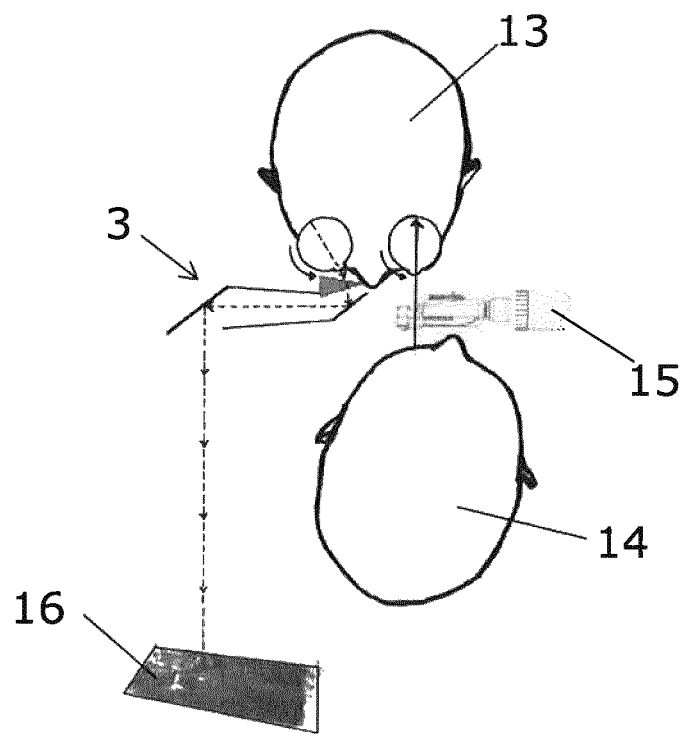
Fig. 2.c

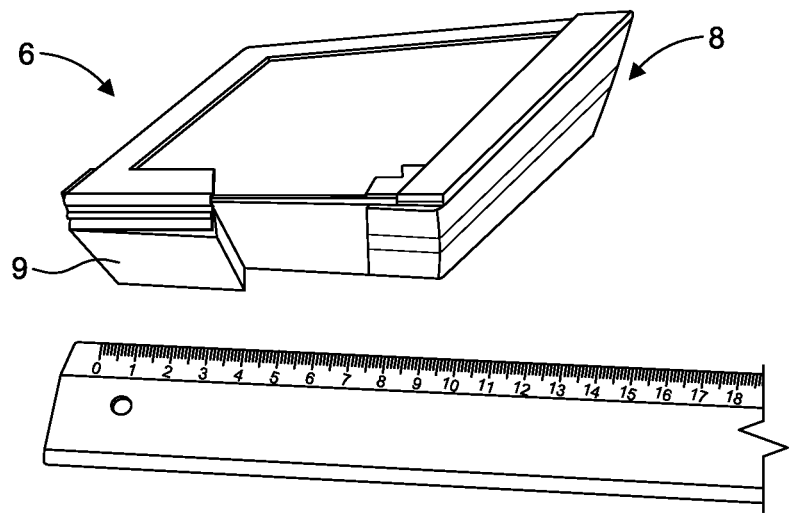
Fig. 5.a
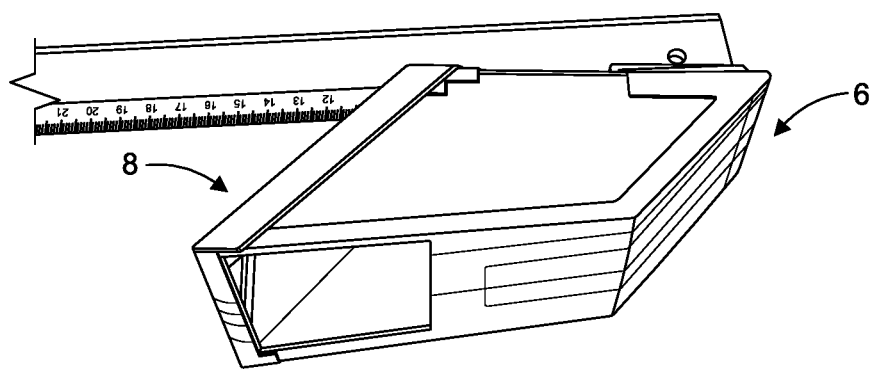
Fig. 5.b

METHOD OF EXAMINING AN EYE OF A SQUINTING PERSON BY USE OF A PERISCOPIC DEVICE AND SUCH A PERISCOPIC DEVICE

FIELD OF THE INVENTION

The present invention relates to a method of examining an eye of an inwardly squinting person (esotropia), and in particular to a method comprising use of a periscopic device. The invention further relates to a periscopic device for use in such method.

BACKGROUND OF THE INVENTION

When a person has his or her eyes examined, e.g. by an ophthalmologist using an ophthalmoscope or a slit lamp microscope, the eye to be examined should preferably be kept still in a desired orientation. When examining a small child, the child often finds it difficult to concentrate and focus the eye in one direction for long enough time. This problem is typically addressed by letting the child watch a film, a flashing light or an interesting toy. However, if the child squints in an inwards direction, the ophthalmologist or an instrument used for examination of the other eye blocks the line of sight of the focusing eye, i.e. the eye not being examined but being used to watch e.g. the film. Instead it must be tried to obtain the same effect by other means, such as by trying to convince the child to be quiet which may not be easy. This makes the examination less efficient and sometimes impossible. In the latter case it may become necessary to perform the examination while the child is under general anaesthesia. This both makes the examination more complicated and may also result in undesired side effects. The same problems as mentioned for small children may also be the case for a mentally disabled person of any age.

OBJECT OF THE INVENTION

It is an object of the present invention to provide an improved method for eye examination of an inwardly squinting person which solves the above mentioned problems.

In particular it is an object of the invention to provide a method which makes the examination of the eyes easier in case of small children or mentally disabled persons.

It is a further object of the present invention to provide an alternative to the prior art.

SUMMARY OF THE INVENTION

Thus, the above described object and several other objects are intended to be obtained in a first aspect of the invention by providing a periscopic device for examining an eye of a person having an inwardly squinting eye, the periscopic device comprising:
 a tube,
 a first mirror arranged inside a first end of the tube which end is adapted to be placed near the person's inwardly squinting eye, and
 a second mirror arranged inside a second end of the tube, wherein the first and the second mirrors are each arranged so that when the person looks through the periscopic device with the inwardly squinting eye while the other eye is being examined, the first and the second mirrors each deflects the line of sight of the person by an angle of approximately 90°, and the periscopic device further comprises a base out prism arranged in front of the first mirror so that, during use of the periscopic device, the line of sight of the inwardly squinting eye is deflected towards the first mirror.

By "tube" is preferably meant an outer housing comprising an inner cavity extending at least between the first and second ends of the housing, the inner cavity preferably being tubular shaped. The cross-sectional shape of the inner cavity may e.g. be circular or rectangular. It may e.g. have a shape matching a screen with format 16:9 so that it is easy for a person to watch an image or a film on a screen of this format.

In the above described embodiment of the invention comprising a base out prism, the first and second mirrors are preferably arranged parallel to each other.

A periscopic device comprising a base out prism may also be called a prism-periscope.

It will be understood by the skilled person that in an alternative embodiment of the invention, the first mirror and/or the second mirror may be replaced by prisms arranged so that the same effect is obtained as in the above described embodiment comprising mirrors.

In a presently preferred embodiment of the invention, the base-out prism is arranged inside the first end of the tube. However, it may also be arranged outside the tube.

In a second aspect of the invention, the above described object and several other objects are intended to be obtained by providing a periscopic device for examining an eye of a person having an inwardly squinting eye, the periscopic device comprising:
 a tube,
 a first mirror arranged inside a first end of the tube which end is adapted to be placed near the person's inwardly squinting eye, and
 a second mirror arranged inside a second end of the tube, wherein the first and the second mirrors are arranged non-parallel to each other, the first mirror being arranged so that when the person looks through the periscopic device with the inwardly squinting eye while the other eye is being examined, the line of sight of the inwardly squinting eye is reflected in the first mirror and towards the second mirror.

The periscopic device as described above and in the following may alternatively be used for the examination of the inwardly squinting eye. This will be explained in further details in relation to the below description of a method according to the invention as well as in the detailed description of the figures.

In some embodiments of the invention, the periscopic device is a combination of a base out prism and mirrors. The person looking through the tube views e.g. a movie through a base out prism, typically 30-45 Prism Diopters, mounted at the patient's end of the tube. This base out prism deflects the light 15-22.5 degrees. The rest of the tube is designed as a traditional periscope with two mirrors typically arranged at 45 degrees and 45 degrees. In total, the line of vision is only deflected as much as the base out prism provides; in a preferred embodiment approximately 20 degrees. The periscopic device according to the invention typically moves the line of sight approximately 10 cm to one side, and thus it is possible to provide room for examining the other eye at the same time.

Such a periscopic device is particularly useful for keeping the person focusing in a desired orientation and also keeping the head still to ease the examination of the eye. This is particularly advantageous for small children or mentally disabled persons who typically find it hard to concentrate for more than a short period of time. The end-users of such a periscopic device are typically people employed in an ophthalmology practice, e.g. eye doctors, nurses, ophthalmic assistants, ophthalmology assisted people, employees in a spectacle shop or anyone who needs the person to focus with one eye while the other eye is examined. The periscopic device can e.g. be used as a fixating device to help obtaining photography of the anterior part of the eye, of the optic nerve or reting, or when performing optic coherence scans of the eyes of the person.

The base out prism may have a prism dioptre between 20 and 50, such as between 30 and 45. "Prism dioptre (PD)" is preferably defined as the unit measuring the deflection of light passing through an ophthalmic prism equal to a deflection of 1 cm at a distance of 1 m. The presently preferred numbers given above have been found to be suitable for the typical degree of squinting seen for persons for which this invention is found advantageous. The periscopic device can also be used when examining children without an inward squint. The periscopic device will enable the examiner to examine one eye while the child focuses with the other eye through the periscopic device.

The cross section of the tube could be of any desired shape, such as circular or quadratic. For some embodiments, the tube may have a substantially constant cross section, and a characteristic dimension of the cross section may be 10 to 60 mm, such as 10 to 30 mm or 20 to 50 mm. In alternative embodiments, the tube may be conical and increasing in cross sectional area from the first end towards the second end. The advantage of a conically shaped tube is that the patient's viewing area is larger than if the tube has a substantially constant cross-section. For a periscopic device with a circular and conical tube, it may e.g. have a diameter in the order of 40 mm at the first end and a diameter in the order of 55 mm at the second end. The cross section could also be curved or have sections that would intuitively make the user hold it in a preferred orientation. The outer surface may also comprise means to ease holding the periscopic device, such as a textured surface or having sections provided with a material that counteract slipping, such as a rubber material.

In any of the embodiments described above, the periscopic device may further comprise mounting means at the first end for mounting the periscopic device in a standard glass frame. This will facilitate using the periscopic device for persons who have difficulties in holding the periscopic device, such as small children or persons who are disabled in any way. In this way it may also be possible to mount the periscopic device in a glass frame fitting the specific person being examined to ensure that it stays in place.

The mounting means may e.g. be an annular ring made from a resilient polymer material, such as silicone, metal or plastic material.

In preferred embodiments of the invention, the periscopic device as described above is handheld. During use it can be held by the person having an eye examined, or it can be held by another person if necessary.

In a third aspect the present invention relates to a method of examining an eye of a person having an inwardly squinting eye, the method comprising:

allowing the person to look through a periscopic device as described above with the inwardly squinting eye while the other eye is examined, and providing an object to focus on at a location which makes it visible by the eye looking through the periscopic device.

Alternatively, the third aspect of the present invention relates to a method of examining an eye of a person having an inwardly squinting eye, the method comprising:

allowing the person to look through a periscopic device as described above with the non-squinting eye while the inwardly squinting eye is examined, and providing an object to focus on at a location which makes it visible by the eye looking through the periscopic device.

In such methods, the periscopic device used may be any of those mentioned above, and the advantages of such methods would thus be the same as those already mentioned above in relation to the periscopic device.

For the embodiments wherein the periscopic device comprises means for mounting the periscopic device in a standard glass frame, the methods may further comprise the step of mounting the periscopic device in the standard glass frame before the examination is performed. Alternatively, a number of such glass frames may be available having corresponding periscopic devices pre-mounted and ready for use.

The first, second, and third aspects of the present invention may each be combined with any of the other aspects. These and other aspects of the invention will be apparent from and elucidated with reference to the embodiments described hereinafter.

BRIEF DESCRIPTION OF THE FIGURES

The periscopic device and the method of using it for examination of a person's eye according to the invention will now be described in more detail with regard to the accompanying figures. The figures show a few ways of implementing the present invention and is not to be construed as being limiting to other possible embodiments falling within the scope of the attached claim set.

FIG. 2 shows schematically how the present invention solves the above mentioned problems related to the eye examination of a person having an inwardly squinting eye. FIGS. 2.a and 2.b show how the line of sight of the eye not under examination is blocked by the examining person. FIG. 2.c shows how the line of sight is changed by use of the present invention.

FIGS. 5.a and 5.b show photos of a prototype version 2.0 made during the development of the present invention.

DETAILED DESCRIPTION OF AN EMBODIMENT

Figure 1:
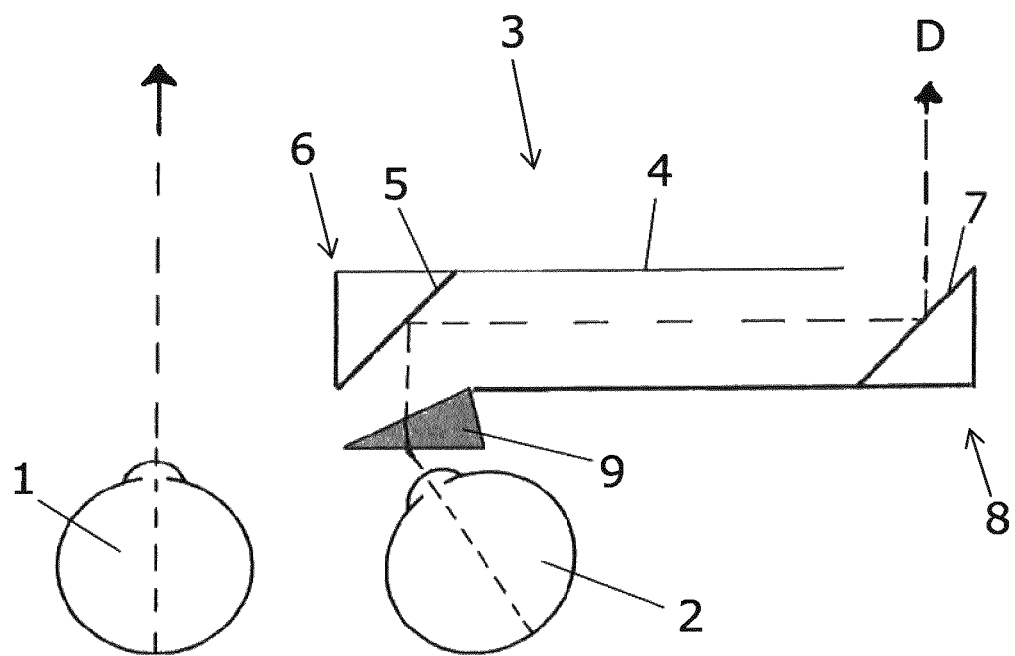
FIG. 1 shows schematically a top view of the principle of an embodiment of the present invention comprising a base out prism.

FIG. 1 shows schematically a top view of the principle of a first embodiment of the present invention used for examining an eye of a person with an inwardly squinting eye (esotropia). In the example shown in the figure, the left eye 1 looks straight ahead while the right eye 2 squints inwards.

When the left eye 1 is to be examined, the periscopic device 3 is placed in front of the right eye 2 which thereby is enabled to focus on e.g. a film at a distance indicated by D in the figure. Hereby it will be easier to keep e.g. a small child still during the examination.

The periscopic device 3 comprises a tube 4 which can be used to hold the periscopic device 3 by the person being examined or a helper, such as a parent. In the embodiment in FIG. 1, the tube is shown with a very simple geometry for illustrative purposes only. The periscopic device may have other geometries and comprise a housing which is easy to hold, such as having the geometry shown in FIG. 6. A first mirror 5 is arranged inside a first end 6 of the tube 4 which end is adapted to be placed near the person's right eye 2 (in the example shown in the figure). A second mirror 7 arranged inside a second end 8 of the tube 4. The periscopic device 3 further comprises a base out prism 9 arranged in front of the first mirror 5 so that, during use of the periscopic device 3, the line of sight of the inwardly squinting right eye 2 is deflected towards the first mirror 5. As can be seen in FIG. 1, it is hereby obtained that the line-of-sight of the inwardly squinting right eye 2 is changed so that it becomes possible to watch an object, such as a film, located at a position D behind the examining ophthalmologist (not shown).

The base out prism 9, the first mirror 5 and the second mirror 7 are each arranged so that when the person looks through the periscopic device 3 with the inwardly squinting eye 2 while the other eye 1 is being examined, the line of sight of the person is deflected by an angle of approximately 20° in total. The embodiment shown in FIG. 1 uses mirrors to deflect the line-of-sight, whereas an alternative may be to use first and second prisms arranged at the first end 6 and the second end 8, respectively. Such prisms must be configured and arranged so that the same effect is obtained.

The tube 4 of the periscopic device 3 shown in cross sectional view in FIG. 1 has a substantially constant cross sections which may e.g. be circular or quadratic. A characteristic dimension of the cross section, such as a diameter or a width, is typically 10 to 60 mm, such as 10 to 30 mm or 20 to 50 mm.

FIG. 2 shows schematically and in a top view how the present invention solves the above mentioned problems related to the eye examination of a person having an inwardly squinting eye. In the figure, the person 13 being examined, and in particular the eyes and the lines of sight, are shown schematically. The examining person 14, such as an ophthalmologist, is shown looking through an instrument 15 which can be any kind of instrument, typically handheld, used for the examination. FIGS. 2.a and 2.b show how the line of sight of the eye not under examination is blocked by the examining person 14 for both of two possible orientations of the instrument 15. Therefore it will not be possible for the person 13 being examined to see an object 16 to focus on arranged at a location behind the examining person 14. Furthermore, FIGS. 2.a and 2.b show that it can be difficult to examine the inwardly squinting eye. FIG. 2.c shows how the periscopic device 3 can be placed in front of the right eye of the person 13 to thereby induce an inward turning of that eye in order to be able to watch the object 16 to focus on through the periscopic device 3. This results in an outward turning of inwardly squinting eye whereby examination thereof is facilitated.

FIG. 2 illustrates the examination of the inwardly squinting eye, but the same periscopic device can correspondingly be used for the examination of the other eye by placing the periscopic device in front of the inwardly squinting eye as was shown in FIG. 1.

Figure 3:
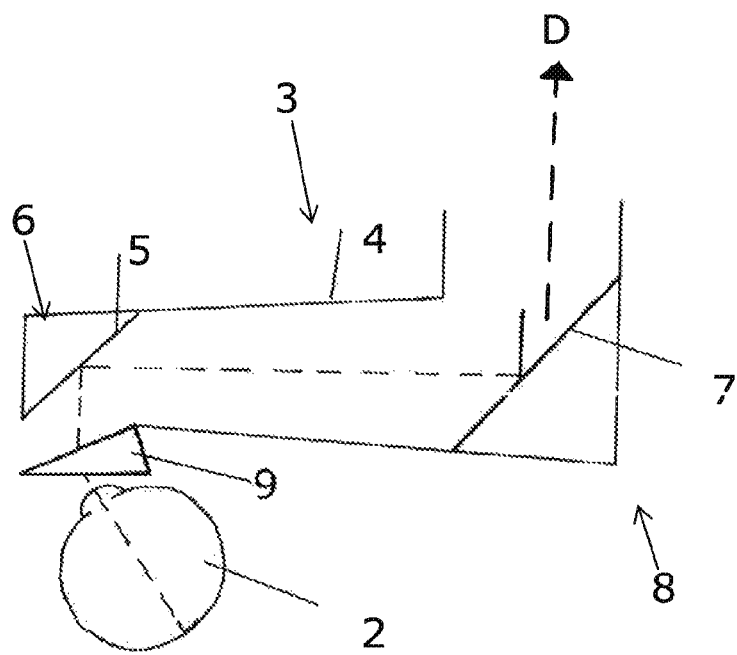
FIG. 3 shows a periscopic device having a tube which is conical and increasing in cross sectional area from the first end towards the second end.

FIG. 3 shows a periscopic device 3 with a tube 4 which is conical and increasing in cross sectional area from the first end 6 towards the second end 8.

Figure 4:
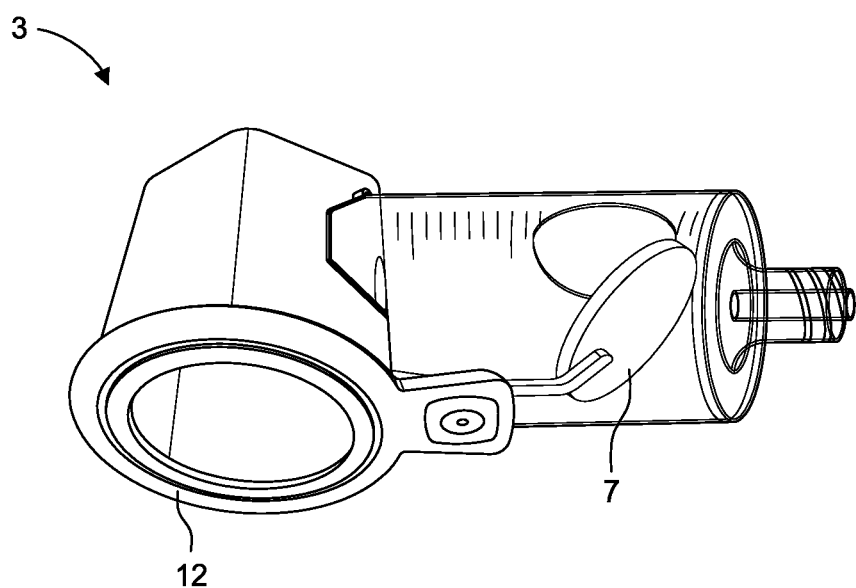
FIG. 4 shows a periscopic device version 1.0 made during the development of the present invention. The periscopic device has mounting means in the form of an annular ring at the first end for mounting the periscopic device in a standard glass frame.

FIG. 4 shows a version 1.0 of the present invention the made during the development thereof. The periscopic device 3 has mounting means 12 in the form of an annular ring at the first end 6 for mounting the periscopic device 3 in a standard glass frame (not shown). Such an annular ring 12 may e.g. be made from a resilient polymer material, such as silicone, or metal or plastic.

FIG. 5 shows photos of a prototype version 2.0. This prototype shown is without the mounting means, but this will be added later. In this embodiment, the tube 4 as shown above is enclosed by a box shaped outer housing, but the working principle is as shown above. The tube 4 as described above may correspond to an open channel through the periscopic device; this is referred to as a tube in the present description. FIG. 5.a shows the periscopic device 3 from the side comprising the base out prism 9; FIG. 5.b shows the periscopic device 3 from the opposite side.

In any of the embodiments shown above, the tube 4 could in principle be made from a number of materials, but in a presently preferred embodiment it is made from plastic. A typical length of a periscopic device 3 would be 10-15 cm.

In a method according to the invention, an examination of an eye of a person having an inwardly squinting eye comprises letting the person look through the periscopic device 3 with the inwardly squinting eye 2 while the other eye 1 is examined. An object 16 to focus on is arranged at a location D which makes it visible by the eye looking through the periscopic device 3; such an object 16 may e.g. be a film or a flashing light. As explained in relation to FIG. 2, the periscopic device 3 can correspondingly be used for the examination of the squinting eye by letting the person look through the periscopic device 3 with the other eye.

So in summary, when combining a traditional periscope with a base out prism 9, it is possible to:

1: examine the eyes of a person with an inward squint (esotropia) as the periscopic device 3 allows the person to focus with the squinting eye while the other non-squinting eye is directed straight forward. The eye pointing straight forward can be examined, and to examine the other eye, the periscopic device 3 is then changed to be held in front of the first examined eye. In this way an inward squinting person can have both eyes examined.

2: The periscopic device 3 according to the present invention allows the examiner 14 to be close to the person 13 without blocking the view of the fixating eye, thus the periscopic device 3 allows the person 13 to "look around" the examiner 14.

Figure 6:
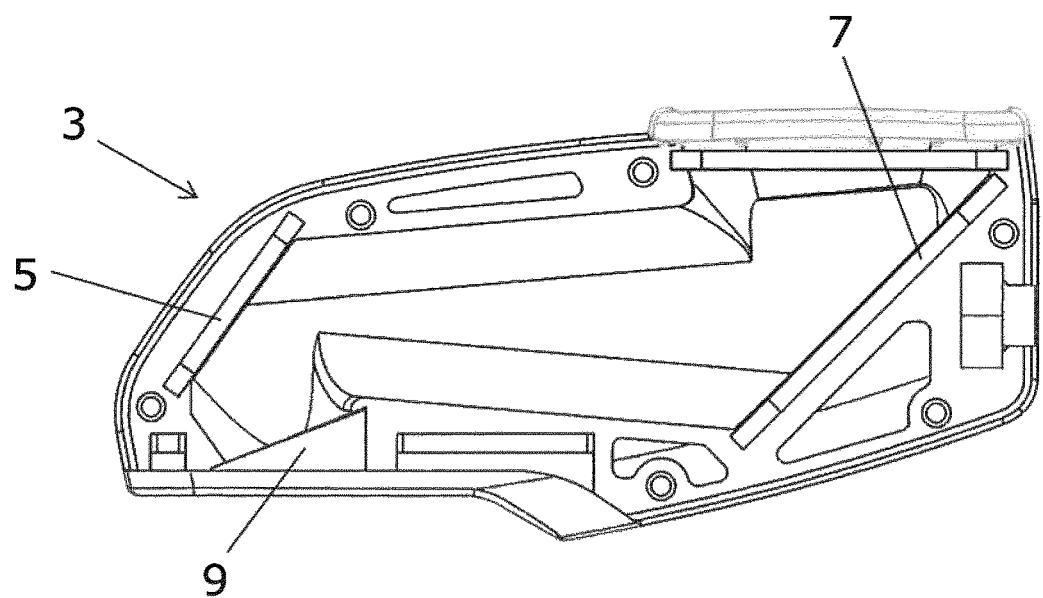
FIG. 6 shows a cross section of an embodiment of the present invention.

FIG. 6 shows a cross section of an embodiment of the present invention comprising a base out prism 9 and in which the tube 4 is conical and increasing in cross sectional area from the first end 6 towards the second end 8. The housing of the periscopic device 3 may e.g. be made by injection moulding, typically of a number of pieces which are subsequently assembled after insertion of the first and second mirrors 5,7 and the base out prism 9.

Figure 7:
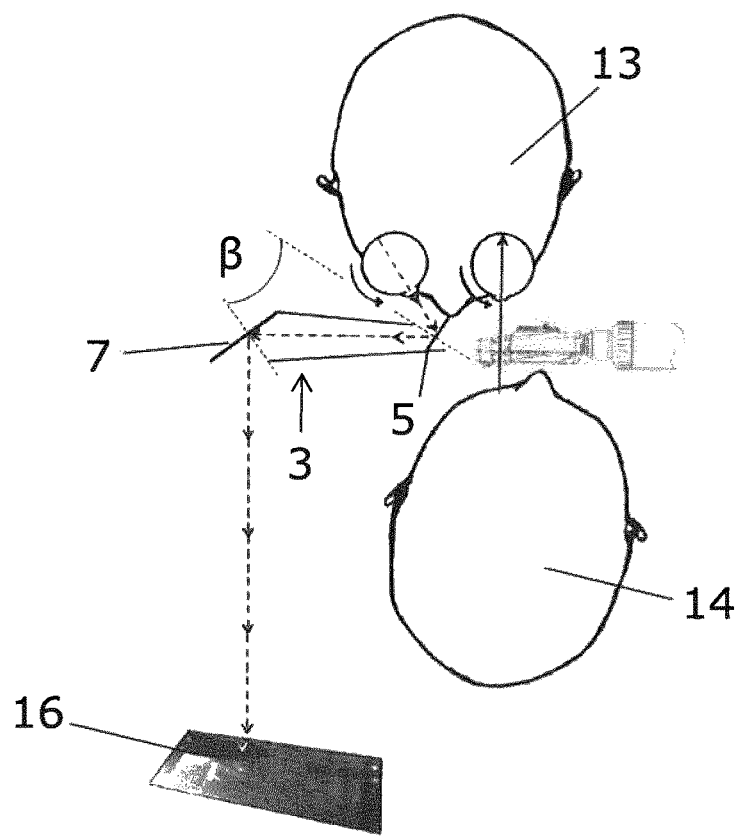
FIG. 7 shows schematically the use of another embodiment of the invention resembling the use shown in FIG. 2.c but with a periscopic device not including a base out prism.

FIG. 7 shows schematically the use of another embodiment of the invention resembling the use shown in FIG. 2.c but with a periscopic device 3 not including a base out prism. In this embodiment, the periscopic device 3 comprises a tube 4, a first mirror 5 arranged inside a first end 6 of the tube 4 which end is adapted to be placed near the person's eye 2, and a second mirror 7 arranged inside a second end 8 of the tube 4. The first and the second mirrors 5,7 are arranged non-parallel to each other, i.e. with and angle β. The angle typically corresponds to the angle of deflection of 15-22.5°, preferably around 20°, as described above for the embodiment with a base out prism. The first mirror 5 is arranged so that when the person looks through the periscopic device 3 with the right eye 2 (in relation to this figure) while the left eye 1 is being examined, the line of sight of the right eye 2 is reflected in the first mirror 5 and towards the second mirror 7. Hereby the same effect is obtained as for the periscopic device 3 comprising a base out prism 9 as described above.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. Periscopic device for examining an eye of a person having an inwardly squinting eye, the periscopic device comprising:
    a single tube,
    a first mirror arranged inside a first end of the tube which end is adapted to be placed near the person's one eye, and
    a second mirror arranged inside a second end of the tube, wherein the single tube defines an axis extending through the first and second mirrors, wherein an area extending along the axis away from the tube from the first end and away from the second end is free of obstructions,
    wherein the periscopic device is dimensioned and shaped so that, when in use, the person can look through the periscopic device from the first end of the tube only with the one eye, while the other eye is exposed for being examined,
    wherein the line of sight of the one eye is reflected in the first mirror and towards the second mirror, and reflected in the second mirror,
    wherein:
        the first and the second mirrors are each arranged so that the first and the second mirrors each deflects the line of sight of the person by an angle of approximately 90°, and the periscopic device further comprises a base out prism arranged in front of the first mirror so that, during use of the periscopic device, the line of sight of the one eye is deflected towards the first mirror, or
        the first and the second mirrors are arranged non-parallel to each other.

2. Periscopic device according to claim 1, wherein the tube is an outer housing comprising an inner cavity extending at least between the first and second ends of the housing.

3. Periscopic device according to claim 1, wherein the one eye with which the person looks through the periscopic device is the inwardly squinting eye.

4. Periscopic device according to claim 1, wherein the periscopic device comprises a base out prism, and wherein the first and second mirrors are arranged substantially parallel to each other and at an angle of 45° in relation to a longitudinal extension of the tube.

5. Periscopic device according to claim 1, wherein the periscopic device comprises a base out prism, the base out prism having a prism dioptre between 20 and 50.

6. Periscopic device according to claim 1, wherein the tube has a substantially constant cross sections, and a characteristic dimension of the cross section is 10 to 60 mm.

7. Periscopic device according to claim 1, wherein the tube is conical and increasing in cross sectional area from the first end towards the second end.

8. Periscopic device according to claim 1 further comprising mounting means at the first end for mounting the periscopic device in a standard glass frame.

9. Periscopic device according claim 8, wherein the mounting means is an annular ring made from a resilient polymer material.

10. Method of examining an eye of a person having an inwardly squinting eye, the method comprising:
    allowing the person to look through the periscopic device according to claim 8 from the first end of the tube only with the inwardly squinting eye, while the other eye which is exposed is examined,
    providing an object to focus on at a location which makes it visible by the inwardly squinting eye looking through the periscopic device, and
    mounting the periscopic device in a standard glass frame before the examination is performed.

11. Periscopic device according to claim 1, wherein the periscopic device is handheld.

12. Periscopic device according to claim 1, wherein the periscopic device comprises a base out prism, the base out prism having a prism dioptre between 30 and 45.

13. Periscopic device according to claim 1, wherein the tube has a substantially constant cross section, and a characteristic dimension of the cross section is 10 to 30 mm.

14. Periscopic device according to claim 1, wherein the tube has a substantially constant cross section, and a characteristic dimension of the cross section is 20 to 50 mm.

15. Method of examining an eye of a person having an inwardly squinting eye, the method comprising:
    providing a periscopic device comprising: a single tube, a first mirror arranged inside a first end of the tube which end is adapted to be placed near the person's one eye, and a second mirror arranged inside a second end of the tube, wherein the periscopic device is dimensioned and shaped so that, when in use, the person can look through the periscopic device from the first end of the tube only with the one eye, while the other eye is exposed for being examined, wherein the line of sight of the one eye is reflected in the first mirror and towards the second mirror, and reflected in the second mirror, wherein: the first and the second mirrors are each arranged so that the first and the second mirrors each deflects the line of sight of the person by an angle of approximately 90°, and the periscopic device further comprises a base out prism arranged in front of the first mirror so that, during use of the periscopic device, the line of sight of the one eye is deflected towards the first mirror, or the first and the second mirrors are arranged non-parallel to each other, allowing the person to look through the provided periscopic device from the first end of the tube only with the inwardly squinting eye, while the other eye which is exposed is examined, and providing an object to focus on at a location which makes it visible by the inwardly squinting eye looking through the periscopic device.

16. Method of examining an eye of a person having an inwardly squinting eye, the method comprising:

providing a periscopic device comprising: a single tube, a first mirror arranged inside a first end of the tube which end is adapted to be placed near the person's one eye, and a second mirror arranged inside a second end of the tube, wherein the periscopic device is dimensioned and shaped so that, when in use, the person can look through the periscopic device from the first end of the tube only with the one eye, while the other eye is exposed for being examined, wherein the line of sight of the one eye is reflected in the first mirror and towards the second mirror, and reflected in the second mirror, wherein: the first and the second mirrors are each arranged so that the first and the second mirrors each deflects the line of sight of the person by an angle of approximately 90°, and the periscopic device further comprises a base out prism arranged in front of the first mirror so that, during use of the periscopic device, the line of sight of the one eye is deflected towards the first mirror, or the first and the second mirrors are arranged non-parallel to each other, allowing the person to look through the provided periscopic device from the first end of the tube only with the non-squinting eye, while the inwardly squinting eye which is exposed is examined, and providing an object to focus on at a location which makes it visible by the non-squinting eye looking through the periscopic device.

17. Method of examining an eye of a person having an inwardly squinting eye, the method comprising:

providing an object to focus on;

providing a periscopic device comprising: a tube, a first mirror arranged inside a first end of the tube which end is adapted to be placed near the person's one eye, and a second mirror arranged inside a second end of the tube, wherein the line of sight of the one eye looking through the first end is reflected in the first mirror and towards the second mirror, and reflected in the second mirror, wherein: the first and the second mirrors are each arranged so that the first and the second mirrors each deflects the line of sight of the person by an angle of approximately 90°, and the periscopic device further comprises a base out prism arranged in front of the first mirror so that, during use of the periscopic device, the line of sight of the one eye is deflected towards the first mirror, or the first and the second mirrors are arranged non-parallel to each other covering the inwardly squinting eye with the first end of the tube of the periscopic device so that the inwardly squinting eye is looking through the periscopic device at the object to focus on; and examining a non-inwardly squinting eye, wherein a doctor's head is positioned in front of the non-inwardly squinting eye while examining the non-inwardly squinting eye.

18. Method of claim 17, further comprising:

moving the periscopic device and uncovering the inwardly squinting eye;

covering the non-inwardly squinting eye with the first end of the tube so that the non-inwardly squinting eye is looking through the periscopic device at the object to focus on; and examining the inwardly squinting eye, wherein the doctor's head is positioned in front of the inwardly squinting eye while examining the inwardly squinting eye.

* * * * *